US008852175B2

(12) United States Patent
Brownell (10) Patent No.: US 8,852,175 B2
(45) Date of Patent: Oct. 7, 2014

(54) APPARATUS, SYSTEM AND METHOD FOR PRECISION DEPTH MEASUREMENT

(75) Inventor: Michael Brownell, San Clemente, CA (US)

(73) Assignee: AMO Development LLC, Santa Ana, CA (US)

( * ) Notice: Subject to any disclaimer, the term of this patent is extended or adjusted under 35 U.S.C. 154(b) by 1121 days.

(21) Appl. No.: 12/275,518

(22) Filed: Nov. 21, 2008

(65) Prior Publication Data

US 2010/0130966 A1   May 27, 2010

(51) Int. Cl.
*A61B 18/18* (2006.01)
*A61B 3/10* (2006.01)
*A61F 9/008* (2006.01)

(52) U.S. Cl.
CPC ..... *A61B 3/1005* (2013.01); *A61F 2009/00872* (2013.01); *A61F 9/008* (2013.01); *A61F 2009/00897* (2013.01)
USPC .......................................................... 606/4

(58) Field of Classification Search
USPC .......................................................... 606/4–6
See application file for complete search history.

(56) References Cited

U.S. PATENT DOCUMENTS

| | | | |
|---|---|---|---|
| 4,764,930 A | 8/1988 | Bille et al. | |
| 5,227,861 A * | 7/1993 | Nishizawa et al. | 356/497 |
| 5,294,289 A | 3/1994 | Heinz et al. | |
| 5,323,229 A * | 6/1994 | May et al. | 356/479 |
| 5,355,209 A * | 10/1994 | Grosso | 356/73.1 |
| 5,365,340 A * | 11/1994 | Ledger | 356/504 |
| 5,404,884 A * | 4/1995 | Lempert | 600/476 |
| 5,549,632 A | 8/1996 | Lai | |
| 5,993,438 A | 11/1999 | Juhasz et al. | |
| 6,254,595 B1 | 7/2001 | Juhasz et al. | |
| RE37,585 E | 3/2002 | Mourou et al. | |
| 6,454,761 B1 * | 9/2002 | Freedman | 606/5 |
| 6,741,359 B2 * | 5/2004 | Wei et al. | 356/512 |
| 6,863,667 B2 | 3/2005 | Webb et al. | |
| 6,899,707 B2 | 5/2005 | Scholler et al. | |
| 6,992,765 B2 | 1/2006 | Horvath et al. | |
| 7,224,518 B2 * | 5/2007 | Tauser et al. | 359/337.5 |
| 7,251,258 B2 * | 7/2007 | Wise et al. | 372/6 |
| 7,256,894 B2 * | 8/2007 | Chen et al. | 356/497 |
| 7,480,396 B2 * | 1/2009 | Teiwes et al. | 382/117 |
| 7,656,538 B2 * | 2/2010 | Paulus et al. | 356/497 |
| 2004/0070761 A1 * | 4/2004 | Horvath et al. | 356/399 |
| 2005/0192562 A1 | 9/2005 | Loesel et al. | |
| 2006/0106371 A1 * | 5/2006 | Muhlhoff et al. | 606/5 |
| 2007/0073905 A1 * | 3/2007 | Cynthia et al. | 710/1 |
| 2007/0093795 A1 | 4/2007 | Melcher et al. | |
| 2007/0282313 A1 * | 12/2007 | Huang et al. | 606/5 |
| 2008/0287929 A1 * | 11/2008 | Holliday et al. | 606/5 |
| 2009/0005764 A1 * | 1/2009 | Knox et al. | 606/5 |

FOREIGN PATENT DOCUMENTS

WO    2004034894 A1    4/2004

* cited by examiner

*Primary Examiner* — William Thomson
*Assistant Examiner* — John R Downey
(74) *Attorney, Agent, or Firm* — AMO Development LLC (57) ABSTRACT

Systems, apparatus, and methods are disclosed for locating tissue layer transitions within a cornea, including focusing a laser to a laser spot with an energy below a photodisruption threshold of the cornea, varying a position of the focal spot of the laser between an anterior surface of the cornea and a posterior surface of the cornea, and determining one or more transitions of the tissue layers based on a change in harmonic light generated by the laser spot.

5 Claims, 4 Drawing Sheets

APPARATUS, SYSTEM AND METHOD FOR PRECISION DEPTH MEASUREMENT

BACKGROUND OF THE INVENTION

Field of the Invention

The present invention pertains generally to ophthalmic surgery, which is useful for correcting vision deficiencies. More particularly, the present invention pertains to systems and methods for precise depth measurements of corneal layers within the eye.

Corneal shape corrective surgeries are commonly used to treat myopia, hyperopia, astigmatism, and the like. Procedures employing an excimer laser include laser assisted in-situ keratomileusis (LASIK), photo refractive keratectomy (PRK) and laser sub-epithelial keratomileusis (LASEK). During LASIK, a suction ring is typically placed over sclera tissue (the white part of the eye) to firmly hold the eye. A microkeratome with an oscillating steel blade can be used to make a partial incision through the front surface of a cornea and/or to automatically pass across the cornea to create a thin flap of tissue on the front central part of the eye. Alternatively, a femtosecond pulsed laser beam may be used to create a corneal flap. After the suction ring is removed, the flap is lifted to expose tissue for ablation with a laser. The laser is typically programmed to correct a desired amount of visual effect, and directs a laser beam at the exposed tissue. A rapid emission of laser pulses removes very small precise amounts of corneal tissue. In LASIK, one objective is the removal of only stromal tissue with the consequent preservation of anterior corneal tissue (e.g., preservation of the epithelium and Bowman's layer). After irrigation with saline solution, the corneal flap is folded back to heal in the pre-procedure or original position.

The flap incision is typically made to a depth below Bowman's layer, for example, to ensure exposure of the stroma when the flap is lifted back. Bowman's layer may be difficult to identify, so many conventional procedures incise the flap at a pre-determined constant depth or distance from the anterior surface of the cornea or optionally from an aplanation lens that might be used to contact the cornea. This depth or distance may be derived from a historical or population based average of corneal thicknesses and may also include a buffer depth. Because some corneas have an irregular thickness profile, some of these incision depths are conservatively pre-determined and can result in deep incisions into the stroma that incise more stromal tissue than is typically needed to form the flap. A remaining stromal layer (i.e., the flap bed following the flap incision) that is too thin may interfere with a desired ablation of the stroma for vision correction.

In light of the above, it would be desirable to provide systems, apparatus, and methods for accurately measuring depths within the cornea for vision correction procedures. It would also be desirable to provide accurate depth measurements for use with producing corneal flap incisions below Bowman's layer while preserving or maximizing the amount of remaining stromal material (e.g., in the flap bed) for vision correction.

BRIEF SUMMARY OF THE INVENTION

Method, system, and apparatus are disclosed for locating tissue layer transitions within a cornea. A laser beam is focused to a laser spot having an energy below a photodisruption threshold of the cornea, the position of the laser spot is varied between an anterior surface of the cornea and a posterior surface of the cornea, and a transition of the tissue layers is determined based on a change in harmonic light generated by the laser spot. The determination of one or more tissue layer transitions can be used to calibrate the system, the laser beam focus, and/or the position of the laser spot.

In one embodiment, a method of locating tissue layers within a cornea is provided, the method including focusing a laser beam to a laser spot having an energy below the photodisruption threshold of the cornea, varying a position of the laser spot between the anterior surface of the cornea and the posterior surface of the cornea, and determining a transition of the tissue layers based on a predetermined change in a harmonic signal. The laser beam has a pre-determined wavelength, and the harmonic signal, based on the pre-determined wavelength, is produced as the laser spot propagates in the cornea.

In another embodiment, a system is provided for locating tissue layer transitions within a cornea. The system includes a laser subsystem configured to scan a laser spot between the anterior surface of the cornea and the posterior surface of the cornea, a sensor configured to detect a harmonic signal, and a processor coupled to the sensor and the laser subsystem. The laser spot has an energy below the photodisruption threshold, and the harmonic signal is produced as the laser spot propagates in the cornea. The processor is configured to monitor a location of the laser spot within the cornea, measure a predetermined change in the harmonic signal, and correlate the location of the laser spot within the cornea with the change in the harmonic signal to determine a tissue layer transition within the cornea.

In another embodiment, an apparatus is provided for determining a depth measurement and incising a cornea. The apparatus includes a first input operable to receive a first input signal indicating a focal depth of a laser beam within the cornea, a second input operable to receive a second input signal representing a harmonic of the laser beam generated as the laser beam propagates in the cornea, an output, and a processor coupled to the first input, the second input, and the output. The laser beam has an energy below the photodisruption threshold. The processor is configured to detect a pre-determined change in the second input signal, correlate the focal depth of the laser beam with a tissue layer transition to provide a reference depth of the laser beam, and transmit an output signal via the output, the output signal indicating the reference depth of the laser beam. The pre-determined change indicates the tissue layer interface within the cornea.

BRIEF DESCRIPTION OF THE DRAWINGS

In the drawings, wherein like reference numerals refer to similar components.

DETAILED DESCRIPTION OF THE INVENTION

The present invention provides systems, apparatus, and methods for precision depth measurements within the eye, particularly the cornea. In one embodiment, a femtosecond laser is used to output a beam having a predetermined wavelength to generate a harmonic thereof when propagating in the corneal tissue. For depth measurement purposes, the beam preferably has an energy below a photodisruption threshold associated with the corneal tissue. The focal spot of the beam is scanned at varying depths within the cornea, and the intensity of the harmonic is detected and monitored for predetermined changes. These changes correspond with tissue interfaces in the cornea and can be used to precisely located tissue layers within the cornea, calibrate the focal depth of the beam, determine the thickness of various tissue layers of the cornea, create two or three dimensional maps of the corneal tissue, and the like. Additionally, this information can be further used to precisely locate incisions formed by the beam.

In some vision correction surgeries, the cornea is incised to form a corneal flap and expose the stroma (e.g., the flap bed being a stromal bed) for refractive correction. The depth of the flap incision is preferably selected to preserve stroma for photoalteration (e.g., such as ablation in laser vision correction surgery) or other modifications to the stroma to effect refractive correction. For example, the average thickness of the cornea is approximately 500 microns at the center of the cornea, the average thickness of the stroma is approximately 450 microns at the center of the cornea (e.g., accounting for approximately 90% of the cornea), the average thickness of the epithelium is approximately 50 microns, and the average thickness of Bowman's layer is approximately 10 microns. Some conventional femtosecond lasers have an average spot size of about 1 micron, which is insignificant with respect to the average thickness of the stroma. Using the systems, apparatus, and methods of the present invention, corneal incisions may be precisely located to maximize stroma preservation for subsequent modifications.

Figure 1:
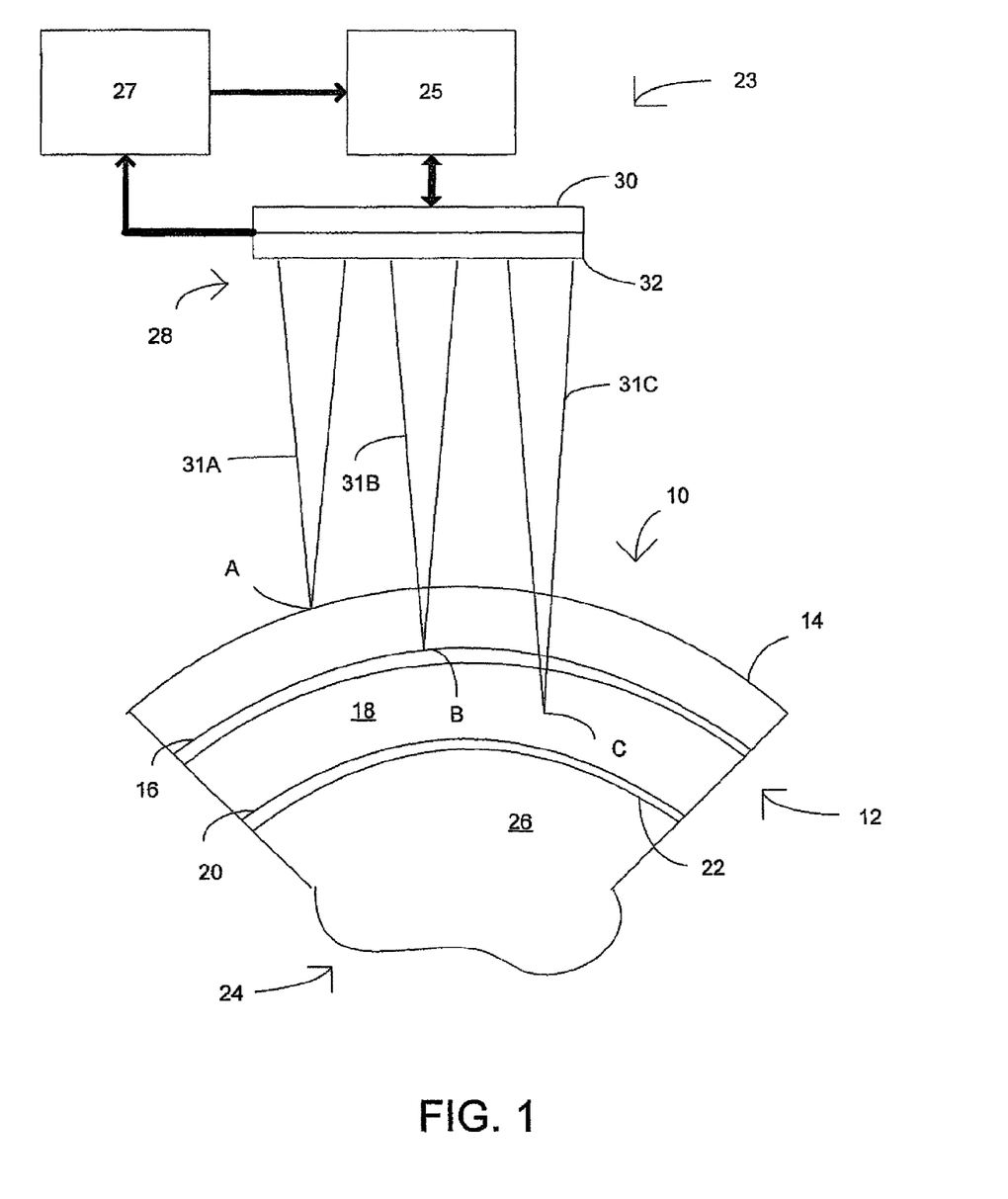
FIG. 1 is a cross-sectional view of a portion of an eye showing anatomical layers of a cornea and a laser system for corneal layer identification and precision depth measurement in accordance with one embodiment.

FIG. 1 is a cross-sectional view of a portion of an eye 10 showing anatomical layers of a cornea 12 and a system 23 for corneal layer identification and precision depth measurement in accordance with one embodiment. In general, the cornea 12 includes five anatomical layers of tissue (not drawn to scale) including the epithelium 14, Bowman's layer 16, the stroma 18, Descemet's membrane 20, and the endothelium 22. Portions of the stroma 18 are typically removed during laser vision correction of the patient's vision (e.g., laser assisted in-situ keratomileusis (LASIK), photo refractive keratectomy (PRK), laser sub-epithelial keratomileusis (LASEK), and the like). The eye 10 also has an anterior chamber 24 cavity filled with aqueous humor 26, and the pressure exerted by the aqueous humor 26 generally maintains the shape of the cornea 12.

The system 23 includes a controller 25, a laser subsystem 28 (e.g., a femtosecond laser) coupled to the controller 25, and a sensor 30 coupled to the controller 25. The laser subsystem 28 outputs and scans a pulsed laser beam at a desired target (e.g., corneal tissue) in response to the controller 25. In addition to managing the operation of the laser subsystem 28 (e.g., beam scanning, scan rate, focal spot depth variation of the pulsed laser beam, and the like), the controller 25 establishes the properties/characteristics of the pulsed laser beam (e.g., pulse energy setting, pulse width setting, and the like).

One example of an ophthalmic laser surgery system where the system 23 may be implemented is described in U.S. Pat. No. 7,027,233, the entire disclosure of which is incorporated herein.

The controller 25 includes computer hardware and/or software, often including one or more programmable processor unit running machine readable program instructions or code for implementing some or all of one or more of the methods described herein. In one embodiment, the code is embodied in a tangible media such as a memory (optionally a read only memory, a random access memory, a non-volatile memory, or the like) and/or a recording media (such as a floppy disk, a hard drive, a CD, a DVD, a memory stick, or the like). The code and/or associated data and signals may also be transmitted to or from the controller 25 via a network connection (such as a wireless network, an Ethernet, an internet, an intranet, or the like), and some or all of the code may also be transmitted between components of the system 23 and within the controller 25 via one or more bus, and appropriate standard or proprietary communications cards, connectors, cables, and the like can be included in the controller 25.

The controller 25 is preferably configured to perform the calculations and signal transmission steps described herein at least in part by programming the controller 25 with the software code, which may be written as a single program, a series of separate subroutines or related programs, or the like. The controller 25 may include standard or proprietary digital and/or analog signal processing hardware, software, and/or firmware, and has sufficient processing power to perform the calculations described herein during treatment of the patient. The controller 25 optionally includes a personal computer, a notebook computer, a tablet computer, a proprietary processing unit, or a combination thereof. Standard or proprietary input devices (such as a mouse, keyboard, touchscreen, joystick, etc.) and output devices (such as a printer, speakers, display, etc.) associated with modern computer systems may also be included, and processors having a plurality of processing units (or even separate computers) may be employed in a wide range of centralized or distributed data processing architectures.

In a first mode, the controller 25 and laser subsystem 28 provide precision depth measurements (i.e., using a pulse energy setting below the photoalteration threshold of the tissue) without photoaltering the corneal tissue. Although the system 23 has a non-photoaltering mode, the system 23 can also be a surgical instrument. For example, in a second mode, the controller 25 and laser subsystem 28 photoalter tissue in accordance with a desired ophthalmic procedure (e.g., corneal flap incision, LASIK, PRK, LASEK, corneal transplant, and the like). The controller 25 and laser subsystem 28 may operate in both modes simultaneously (e.g., providing real time depth measurement, laser beam focal spot depth calibration, and the like) or seamlessly alternate between the two modes.

To provide the pulsed laser beam, the laser subsystem 38 may use a chirped pulse laser amplification system, such as described in U.S. Pat. No. RE37,585. Other devices or systems may be used to generate pulsed laser beams. For example, non-ultraviolet (UV), ultrashort pulsed laser technology can produce pulsed laser beams having pulse durations measured in femtoseconds. U.S. Pat. Nos. 4,764,930 and 5,993,438, the entire disclosures of which are incorporated herein, disclose devices for performing ophthalmic surgical procedures to effect high-accuracy corrections of optical aberrations. The laser subsystem 28 is capable of generating a pulsed laser beam with characteristics similar to those of the laser beams generated by a laser system disclosed in U.S. Pat. Nos. 4,764,930, 5,993,438, or the like.

For example, the system 23 can produce a non-UV, ultrashort pulsed laser beam for use as an incising laser beam. This pulsed laser beam preferably has laser pulses with durations as long as a few nanoseconds or as short as a few femtoseconds. The pulsed laser beam has a wavelength that permits propagation through the cornea without absorption by the corneal tissue, except at the focal spot of the pulsed laser beam. The wavelength of the pulsed laser beam is generally in the range of about 3 µm to about 1.9 nm, and preferably between about 400 nm to about 3000 nm. For depth measurement, the irradiance of the pulsed laser beam is preferably less than the threshold for optical breakdown of the tissue. For accomplishing photodisruption of stromal tissues at the focal spot or for incising corneal tissue in general (e.g., in the second mode), the irradiance of the pulsed laser beam is selected to be greater than the threshold for optical breakdown of the tissue. Although a non-UV, ultrashort pulsed laser beam is described in this embodiment, the pulsed laser beam may have other pulse durations and different wavelengths in other embodiments.

Scanning by the laser subsystem 28 is accomplished under direction of the controller 25 to selectively move the focal spot of the laser beam. The laser subsystem 28 can operate at scan rates between about 10 kHz and about 400 kHz, or at any other desired scan rate. Further details of laser scanning are known in the art, such as described, for example, in U.S. Pat. No. 5,549,632, the entire disclosure of which is incorporated herein by reference. For example, a pair of scanning mirrors or other optics may be used to angularly deflect and scan one or more input beams. The scanning mirrors may be driven by galvanometers such that each of the mirrors scans along different orthogonal axes (e.g., an x-axis and a y-axis). A focusing objective (not shown), having one or more lenses, images the input beam onto a focal plane of the system 23. The focal spot may thus be scanned in two dimensions (e.g., along the x-axis and the y-axis) within the focal plane of the system 23. Scanning along the third dimension, i.e., moving the focal plane along an optical axis (e.g., a z-axis), may be achieved by moving a focusing objective, or one or more lenses within the focusing objective, along the optical axis.

The system 23 may additionally acquire detailed information about optical aberrations to be corrected or verify/correlate the depth measurements with such detailed information (e.g., data registration). Examples of such detailed information include, but are not necessarily limited to, refractive power maps of the cornea, corneal topography, iris registration information, and the like. Wavefront analysis techniques, made possible by devices such as a Hartmann-Shack type sensor, can be used to generate maps of corneal refractive power, and optical coherence tomography may be used to generate corneal topographs. Other wavefront analysis techniques and sensors may also be used.

During the first mode, the laser subsystem 28 outputs a pulsed laser beam having predetermined properties associated with the generation of a nonlinear frequency signal based on the pulsed laser beam (e.g., a non-primary harmonic of the pulsed laser beam such as a second harmonic generation, a third harmonic generation, stimulated Raman, white light generation, and the like) during propagation of the pulsed laser beam in the cornea 12. On example of harmonic signal generation based on a laser beam is disclosed in U.S. Pat. No. 6,992,765. In this patent, a method is disclosed for determining the depth of focus of a laser beam in relation to the plane of an aplanation lens by monitoring a nonlinear frequency signal generated by the laser beam, the disclosure of which is incorporated herein. A change in the signal indicates the interface between lower surfaces of the aplanation glass and the cornea.

The systems, apparatus, and methods of the present invention have advanced, inter alia, the detection of a nonlinear frequency signal generated by the laser beam. In particular, the systems, apparatus, and methods of the present invention detect and identify corneal tissue transitions based the detection of a nonlinear frequency signal generated by a pulsed laser beam propagating in corneal tissue. For example, the wavelength of the pulsed laser beam can be selected such that an intensity of the nonlinear frequency signal correlates with the tissue density and type. The nonlinear frequency signal abruptly changes characteristics at a corneal tissue layer transition (e.g., from the epithelium 14 to Bowman's layer 16, from Bowman's layer 16 to stroma 18, from stroma 18 to Descemet's membrane 20, etc.). In one embodiment, an optimal wavelength is selected to maximize this change and enhance the detection of one or more corneal tissue layer transitions.

As previously mentioned, incisions to access the stroma 18 are preferably located so as to maximize the amount of stroma for refractive correction (e.g., ablation and the like). For example, the incision is proximally located adjacent to Bowman's layer 16 to maximize the amount of stroma for refractive correction. In one embodiment, the depth of Bowman's layer 16 is precisely determined in the first mode, and the cornea 12 is incised at a depth below Bowman's layer 16 (e.g., to form a flap bed associated with the corneal flap) in the second mode.

For a precision depth measurement (e.g., the depth of Bowman's layer or other corneal tissue layers), the pulsed laser beam is focused to a focal spot with an energy less than the threshold for optical breakdown of the tissue, and the focal spot is scanned at various depths within the cornea 12. For example, the focal spot is scanned along the optical axis (e.g., z-axis), which may be normal to the anterior surface of the cornea or aligned in accordance with a pre-determined scan pattern. In one experiment, a pulsed laser beam with an energy level of about 0.2 µJ was directed into the cornea so that the corresponding fluence was less than the optical damage threshold (see U.S. Pat. No. 6,992,765 for some examples of other energy levels that are less than the optical damage threshold of the cornea).

As the focal spot is scanned in the cornea 12, a harmonic of the beam is generated in the corneal tissue (e.g., a green harmonic wavelength or the like). For example, a second harmonic is generated in the corneal tissue based on a primary wavelength of the pulsed laser beam. The sensor 30 (e.g., a photodetector) detects and measures the harmonic generated by the propagation of the pulsed laser beam in the cornea 12. In one embodiment, the sensor 30 is configured to receive the harmonic using an optical bandpass filter with a filter bandwidth sufficient for detecting the harmonic wavelength, although other sensing devices may be used to detect the harmonic.

One or more parameters of the pulsed laser beam (e.g., pulse width, wavelength, energy, and the like) may be selected such that the detected harmonic indicates an optimal change in intensity at a tissue layer transition. Additionally, one or more of the pulsed laser beam parameters may be selected such that different predetermined changes in intensity (i.e., of the detected harmonic) are produced corresponding with different tissue laser transitions. For example, the pulsed laser beam parameter(s) may be selected such that a first intensity change in the detected harmonic corresponds with a transition from the epithelium 14 to Bowman's layer 16, a second intensity change in the detected harmonic corresponds with a transition from Bowman's layer 16 to stroma 18, a third intensity change in the detected harmonic corresponds with a transition from stroma 18 to Descemet's membrane 20, and a fourth intensity change in the detected harmonic corresponds with a transition from Descemet's membrane 20 to the endothelium 22. Other tissue layer transitions (e.g., associated with the cornea 12 or other tissues or structures of the eye 10) may be earmarked for identification based on the detected harmonic and/or by selection of an appropriate pulsed laser beam wavelength.

As shown in FIG. 1, in one embodiment, the laser subsystem 28 directs a pulsed laser beam 31A, 31B, 31C at the cornea 12 and scans the tissue layer depth at varying focal spot positions. Three pulsed laser beams 31A, 31B, 31C are described for convenience of illustrating the variety of placements of the focal spot. For example, a first pulsed laser beam 31A can be focused at focal spot position A, a second pulsed laser beam 31B can be focused at focal spot position B, and a third pulsed laser beam 31C can be focused at a focal spot position C. Position A is at the surface of the epithelium 14, position B is at the transition between the epithelium 14 and Bowman's layer 16, and position C is in the stroma 18. In another embodiment, a single beam is directed into the cornea 12 at the focal spot positions A, B, C or to other different focal spot positions. The focal spot position of the pulsed laser beam may also be continuously varied or incrementally varied (e.g., by predetermined focal spot displacements).

The identification of the tissue layer transition(s) can be used to calibrate the incision depth of the pulsed laser beam before or during refractive surgery procedures. In one embodiment, the system 23 includes a Z-encoder module 27 coupled to the controller 25 and sensor 30, and the Z-encoder module registers the focal spot position (e.g., focal spot depth) of the pulsed laser beam with the corresponding detected tissue layer transition. For example, the Z-encoder module 27 may include a linear encoder having an encoder strip (e.g., a glass strip with a reflective gradient), a sensor head, and an interpolator-to-serial module that indicates the position of the focusing objective or other z-focus assembly. The Z-encoder module 27 preferably has a resolution of about 0.1 microns or less per count at a frequency of about 900 MHz or greater. With the encoder strip coupled to the focusing objective, the position of focusing objective or z-focus assembly can be determined using the linear encoder, and the focal spot position can be controlled to within a few microns of a predetermined absolute value. Correlating this information with the detected harmonic signal, the focal spot position can be verified and the laser subsystem 28 can be calibrated. This can be used to precisely locate incisions and produce thin corneal flaps, as well as other flap configurations. For example, corneal flap beds can be located in the range of about 20 microns below the epithelium/Bowman's layer tissue transition.

In addition to real-time calibration of the laser subsystem 28, the detection of tissue layer transitions can be used for two- or three-dimensional corneal mapping and the like. For example, an array of the depth measurements over an area of corneal tissue may be used to identify the anatomical layers of the cornea 12, determine the thickness of one or more of such layers, and the like. A variety of scan patterns may be used to obtain multiple depth measurements across the cornea.

Figure 2:
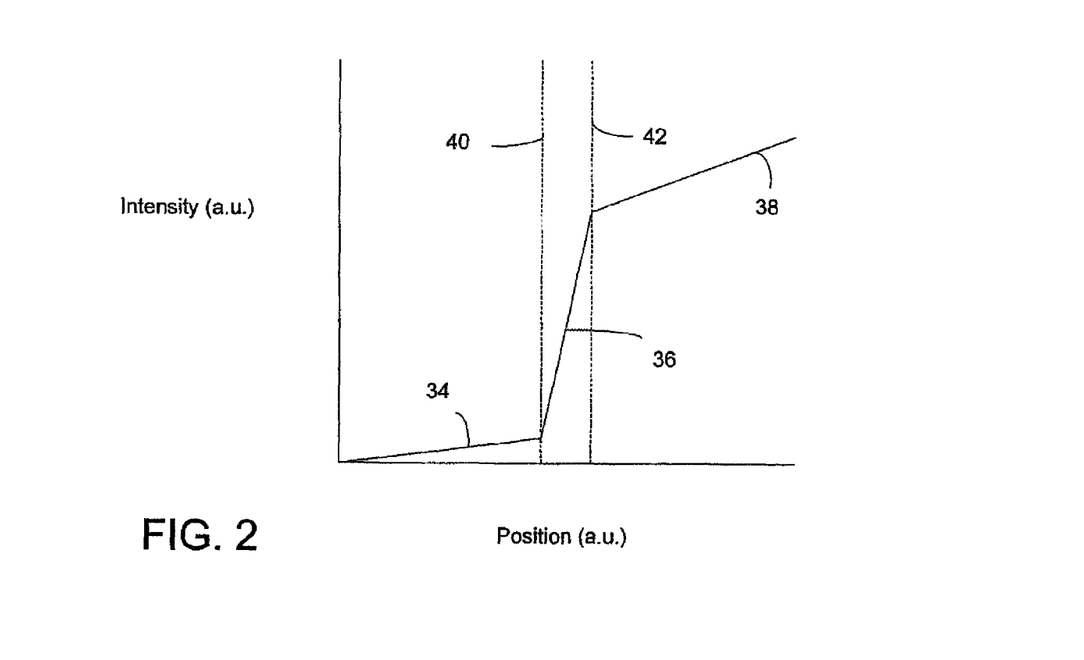
FIG. 2 is a graph of intensity versus position illustrating a relationship of intensity change in a harmonic signal as a function of focal depth within corneal tissue.

FIG. 2 is a graph of intensity versus focal spot position (e.g., focal spot depth along an optical axis) illustrating a relationship of intensity change in a detected harmonic signal as a function of focal spot depth of a pulsed laser beam propagating within corneal tissue in accordance with one embodiment. The intensity and focal spot position are in arbitrary units (a.u.). To obtain the relationship shown in FIG. 2, the focal spot of the pulsed laser beam (e.g., the pulsed laser beam 31A, 31B, 31C, which may be produced by the system 23 show in FIG. 1) is scanned along an optical axis at varying depths of the corneal tissue, and the harmonic signal is detected (e.g., using the sensor 30 shown in FIG. 1). As the focal spot of the pulsed laser beam propagates through the corneal tissue, the intensity of the harmonic signal varies based on the corneal tissue thickness and type. For example, the slope of a first segment 34 represents an intensity change of the harmonic signal as the focal spot position of the pulsed laser beam propagates through the epithelium, the slope of a second segment 36 represents an intensity change of the harmonic signal as the focal spot position of the pulsed laser beam propagates through Bowman's layer, and the slope of a third segment 38 represents the intensity change of the harmonic signal as the focal spot position of the pulsed laser beam propagates through the stroma. The intensity may be a nonlinear interference frequency signal based on the pulsed laser beam, such as a second harmonic generation, a third harmonic generation, a stimulated Raman, a white light generation, or other suitable optical signals.

The position of a transition between corneal tissue layers can be identified by the detection (e.g., via the controller 25) of an abrupt change in the harmonic signal at the transition. For example, in FIG. 2, the epithelium/bowman's transition occurs at a first abrupt change 40, and the Bowman's layer/stroma transition occurs at a second abrupt change 42. The abrupt change can be predetermined based on historical information, corneal tissue models, and the like, for example. The distance between these abrupt changes may also be used to determine the thickness of a particular layer. For example, the thickness of Bowman's layer corresponds with the distance between the first abrupt change 40 and the second abrupt change 42. A position beyond the second abrupt change 42 (shown by arrow 44) is within the stroma. Other graphs may also be prepared illustrating other tissue layer transitions (e.g., from a posterior surface of the cornea or for other structures of the eye) based on corresponding relationships of intensity change in the detected harmonic signal as a function of focal spot depth of the pulsed laser beam.

Figure 3:
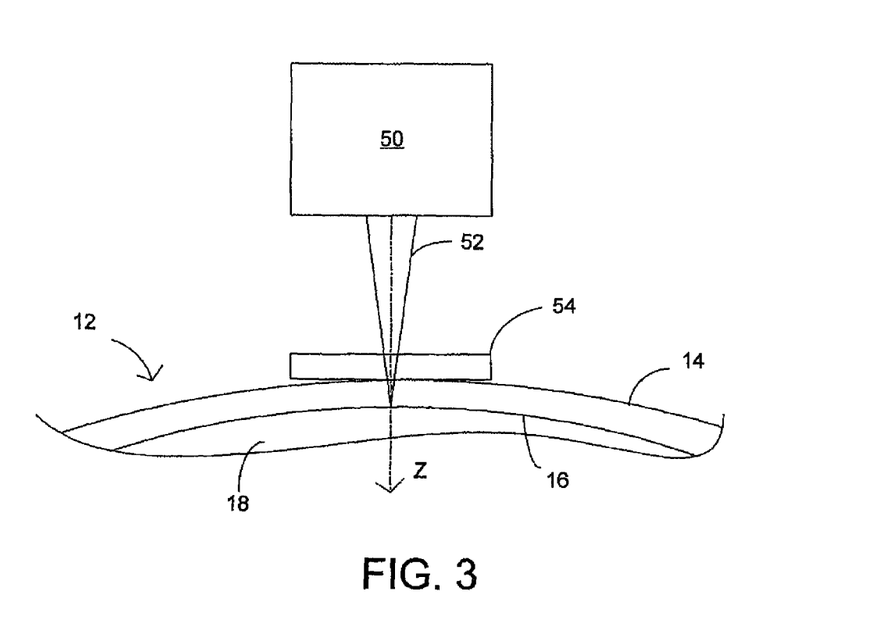
FIG. 3 is a schematic diagram of the laser system used in situ while the eye is in contact with an aplanation lens in accordance with another embodiment.

FIG. 3 is a schematic diagram of a laser system 50 in accordance with another embodiment. While FIG. 1 shows one embodiment of a laser system 23 directing a pulsed laser beam directly into the cornea 12, FIG. 3 shows another embodiment of a laser system 50 used in situ and while the cornea 12 is in contact with an aplanation lens 54. The laser system 50 can be substantially similar to the laser system 23 (shown in FIG. 1) with the additional component of the aplanation lens 54. The aplanation lens 54 can be a flat or curved contact glass with a predetermined thickness, which can provide a reference for thickness measurements of various layers of the cornea 12 or other features of the eye. Examples of aplanation lenses include, by way of example and not limitation, U.S. Pat. Nos. 6,254,595, 6,863,667, 6,899,707, U.S. Pat. Publication No. 20050192562, and U.S. Pat. Publication No. 20070093795. In detecting corneal tissue transitions, the thickness of the aplanation lens 54 is included as a reference depth.

The laser system 50 directs the focal point of a pulsed laser beam 52 through the aplanation lens and into the cornea 12 along the optical axis (e.g., the z-axis). In this embodiment, the laser system 50 is shown scanning the pulsed laser beam 52 along the z-axis in the cornea 12 to detect the transition between the epithelium 14 and Bowman's layer 16. Other corneal tissue layer transitions may also be determined with the pulsed laser beam 52 directed through the aplanation lens 54. A precision Z-calibration can also be performed with the laser system 50 in real time during an ophthalmic procedure on the eye.

Figure 4:
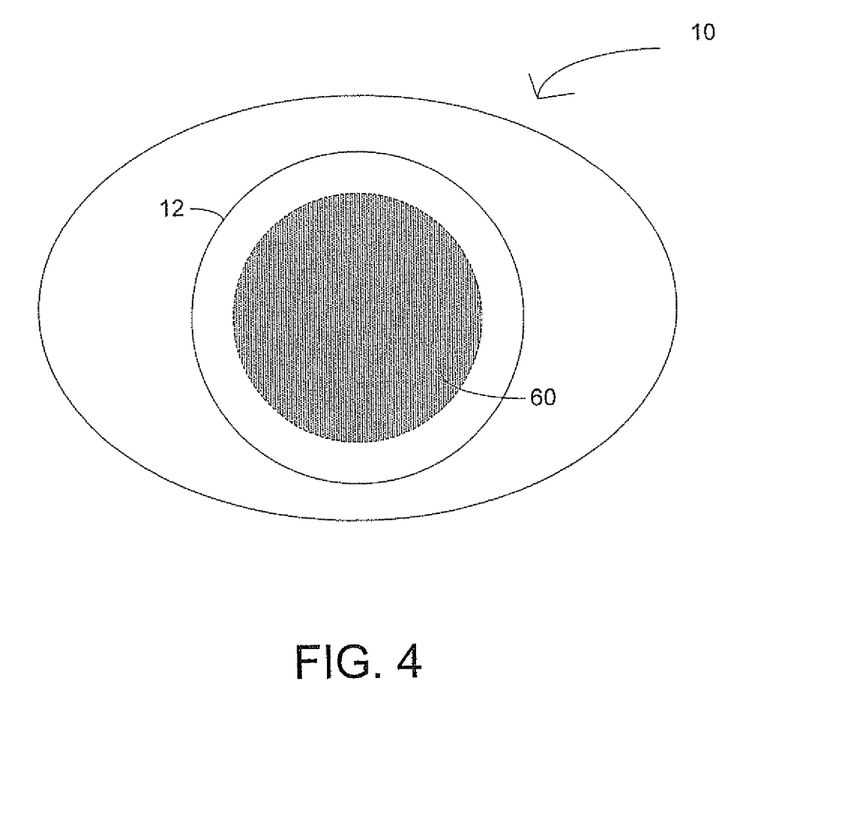
FIG. 4 is a top view of a corneal flap mapped onto a cornea in accordance with one embodiment.

FIG. 4 is a top view of a corneal flap mapped onto the cornea 12 in accordance with one embodiment. As previously mentioned, precision depth measurements (e.g., using the system 23 shown in FIG. 1 or the system 50 shown in FIG. 3) may be taken at various locations across the cornea 12 to create a three-dimensional map of the cornea 12. In this embodiment, Z-calibrated depth measurements are used to determine a precision flap zone 60 from which the system 23, 50 can create a three-dimensional flap map (e.g., with precision on the micron order). The three-dimensional flap map preferably displays the flap incision below the bowman's/stroma interface.

Figures 5, 6, 7:
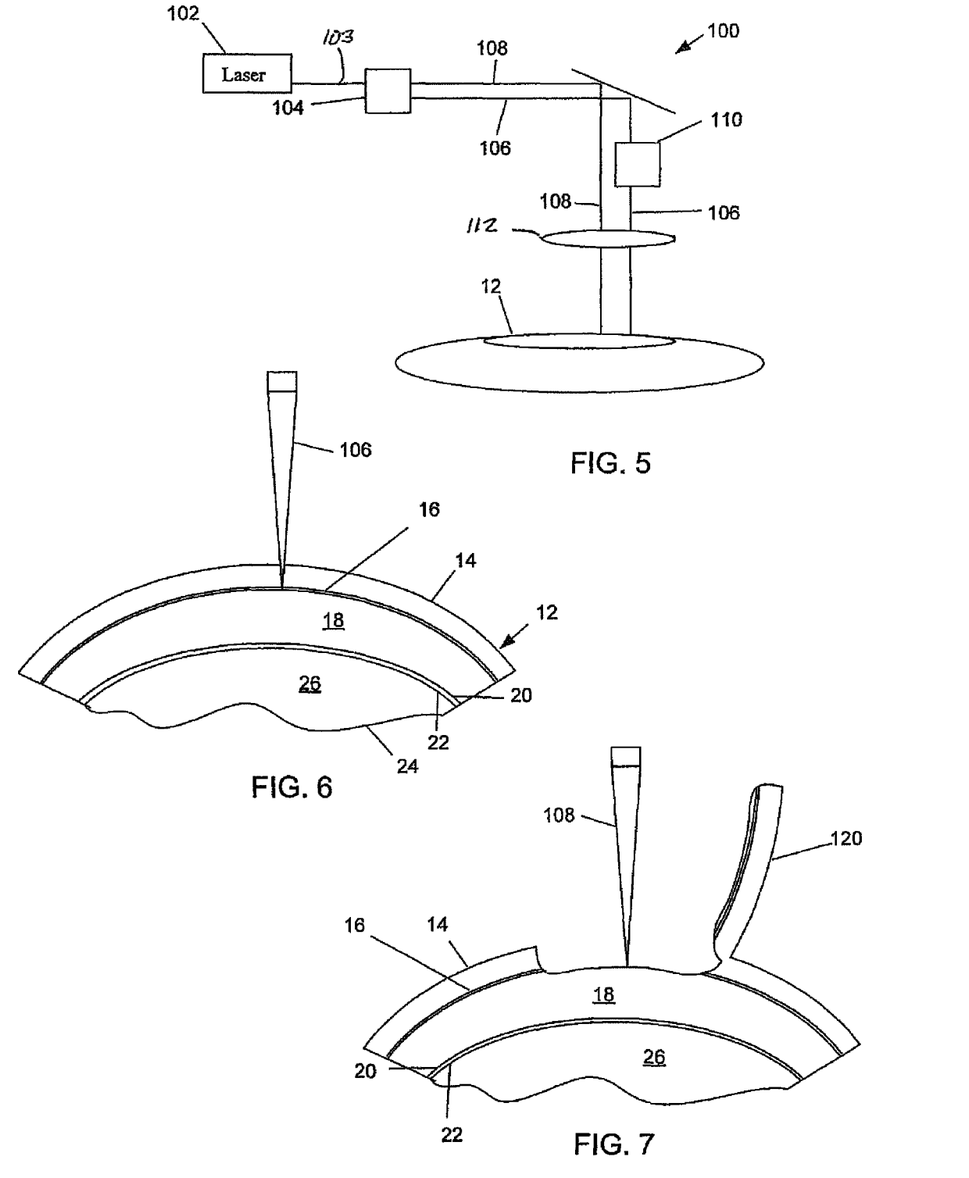
FIG. 5 is a block diagram of a laser system in accordance with another embodiment.
FIG. 6 is a cross-sectional view of the portion of the eye shown in FIG. 1 showing a diagnostic beam scanning the cornea.
FIG. 7 is a cross-sectional view of the portion of the eye shown in FIGS. 1 and 6 showing a surgical beam incising a flap.

FIG. 5 is a block diagram of a laser system 100 in accordance with another embodiment. In this embodiment, the laser system 100 includes a laser 102 that outputs a pulsed laser beam for mapping corneal layers and for incising the cornea (e.g., to form a corneal flap, a lenticule, a corneal graft, and the like), a beam splitting device 104, a z-scanner 110, and a focusing objective 112 (e.g., a focusing lens). The laser 102 may be a femtosecond laser that produces a pulsed laser beam 103, as previously described. The pulsed laser beam 103 is directed to the beam splitting device 104, which divides the pulsed laser beam 103 into a first beam 106 and a second beam 108.

The first beam 106 is a diagnostic beam having focused energies less than the photodisruption threshold of the cornea 12 and is used for corneal mapping to identify the different layers within the cornea 12. For example, by varying the focal spot position of the beam 106 across the cornea 12 using the scanner 110 and varying the focal spot depth using the z-scanner 110, the first beam 106 is scanned through the cornea 12 to detect the harmonic of the laser beam wavelength. The harmonic of the first beam 106 is used to determine one or more tissue layer transitions within the cornea 12 (e.g., between Bowman's layer and stroma) based on a predetermined change in the harmonic as the beam 106 propagates in the corneal tissue. The first beam 106 can also be used to determining a distance from an anterior surface of the cornea 12 to the transition between Bowman's layer and stroma. A buffer depth may be added to this determined distance to provide a planned incision depth that ensures the incision of the corneal flap in the stroma. This buffer depth may range between about 10 and about 40 microns.

The second beam 108 is a surgical beam having focused energies greater than the photodisruption threshold of the cornea 12 and can incise a flap below the Bowman's layer/stroma transition. In some embodiments, the second beam 108 is also used for shaping the stroma (e.g., after the flap is lifted to reveal the flap bed or intrastromally without creating a flap or with the cornea intact). By dividing the beam 104 into two beams 106, 108, the laser system 100 allows a diagnostic beam to be used in real time during an ophthalmic procedure, which provides instantaneous Z control of the surgical beam.

In any of the embodiments, the system 100 may include a processor (e.g., the controller 25 shown in FIG. 1) to control various functions of the system, for example, control a Z-encoder (e.g., the Z-encoder module 27 shown in FIG. 1) or the scanner 110, vary the focal spot position of the beam, process focal spot position information, and the like. The processor may also be coupled to a sensor (e.g., the sensor 30 shown in FIG. 1) that measures the emitted harmonic from the tissue. In this example, the processor determines a tissue layer transition between Bowman's layer and the stroma based on a detected predetermined change in the harmonic (of the laser wavelength) in the cornea tissue and determines a distance from an anterior surface to the transition. The processor may also incorporate the buffer depth to this determined distance to provide the planned incision depth.

FIG. 6 is a cross-sectional view of a portion of the eye 10 showing a diagnostic beam, such as the first beam 106 shown in FIG. 5, scanning the cornea 12. The transition between Bowman's layer 16 and the stroma 18 is identified by varying the focal spot depth of the diagnostic beam 106 (e.g., along the optical axis or the z-axis). A distance can be determined between the tissue layer transition and the anterior surface of the cornea 12. FIG. 7 is a cross-sectional view of a portion of the eye 10 showing a surgical beam, such as the second beam 108 shown in FIG. 5, incising a flap 120 in the stroma below the transition between Bowman's layer 16 and the stroma 18. The flap 120 can be folded back to expose the stroma 18 for further treatment. As shown by FIGS. 5-7, a single laser may be used to produce both the diagnostic beam and the surgical beam and direct one or both of the beams at the eye.

The methods and system 23, 50, 100 described above allow a femtosecond laser to precisely locate incisions and incise extremely thin, precise, accurate, custom corneal flaps. The laser system 23, 50, 100 can also be used as a combined precision measurement tool and ophthalmic surgical instrument.

While the disclosure has been described in connection with specific embodiments thereof, it will be understood that it is capable of further modifications. This application is intended to cover any variations, uses, or adaptations of the disclosure following, in general, the disclosed principles and including such departures from the disclosure as come within known or customary practice within the art to which the disclosure pertains and as may be applied to the essential features hereinbefore set forth.

What is claimed is:

1. A system for locating tissue layer transitions within a cornea having an anterior surface, a posterior surface, and a photodisruption threshold, the system comprising:

a laser subsystem configured to scan a laser spot at varying focal positions between the anterior surface of the cornea and the posterior surface of the cornea, the laser spot having an energy level of 0.2 µJ such that the irradiance of the laser spot is below the photodisruption threshold, a harmonic signal being produced as the laser spot propagates in the cornea, wherein the cornea has adjacent tissue layers with different harmonic signals, the adjacent tissue layers comprising one or more of the group consisting of an epithelium, a Bowman's layer, a stroma, a Descemet's membrane and an endothelium, and wherein the change in the harmonic signal indicates the tissue layer transition;

a sensor configured to detect the harmonic signal; and a processor coupled to the sensor and the laser subsystem, the processor configured to:

monitor a location of the laser spot within the cornea;

measure a change in the harmonic signal; correlate the location of the laser spot within the cornea with the change in the harmonic signal to determine a tissue layer transition within the cornea;

determine a thickness of the tissue layers based on the harmonic signal; and determine a distance between the tissue layer transition and the anterior surface of the cornea or the posterior surface of the cornea;

wherein the laser subsystem comprises a femtosecond laser configured to produce a non-ultraviolet pulsed laser beam with a wavelength of about 400 nm to about 3000 nm, the spot corresponding to a focal spot of the beam; and wherein the harmonic signal has an intensity; and the change in the signal is based on a change in the intensity of the harmonic signal.

2. The system of claim 1, wherein the processor is further configured to generate a three dimensional model of the tissue layers based on the tissue layer transition.

3. The system of claim 1, wherein the laser subsystem is further configured to:
output a pulsed incision beam having a pulse energy of greater than or equal to the photodisruption threshold; and
incise the cornea with the pulsed incision beam based on the tissue layer transition.

4. The system of claim 1, wherein the laser subsystem is further configured to scan a laser spot at varying focal positions continuously.

5. The system of claim 1, wherein the laser subsystem is further configured to scan a laser spot at varying focal positions incrementally.

* * * * *